United States Patent [19]

Stormbom

[11] Patent Number: 5,075,816
[45] Date of Patent: Dec. 24, 1991

[54] CAPACITIVE HUMIDITY SENSOR CONSTRUCTION AND METHOD FOR MANUFACTURING THE SENSOR

[75] Inventor: Lars Stormbom, Vantaa, Finland

[73] Assignee: Vaisala Oy, Helsinki, Finland

[21] Appl. No.: 553,596

[22] Filed: Jul. 18, 1990

[30] Foreign Application Priority Data

Aug. 11, 1989 [FI] Finland ................................ 893797

[51] Int. Cl.[5] .......................... H01G 7/00; G01N 27/12
[52] U.S. Cl. .................................. 361/286; 29/25.42; 73/366.5
[58] Field of Search .......................... 29/25.42; 427/79; 361/286; 73/336.5

[56] References Cited

U.S. PATENT DOCUMENTS 3,614,561 10/1971 Behn et al. ............................ 361/286
4,164,868 8/1979 Suntola ................................ 73/336.5
4,305,112 12/1981 Heywang et al. .................... 361/286
4,761,710 8/1988 Chen ..................................... 361/286

Primary Examiner—Donald A. Griffin

[57] ABSTRACT

The invention concerns a capacitive humidity sensor (6) capable of being connected to a measurement device of dielectric factor and a method for producing the sensor. The sensor comprises a dielectric layer (3), whose dielectric factor changes according to the moisture content absorbed in the layer, and at least two galvanically isolated conductive layers (2,1) enclosing the dielectric layer (3), where one of the conductive layers (2) of the capacitor construction is provided with a random pattern of clefts (7), which allow an immediate communication of ambient air with the dielectric layer (3). According to the invention, the dielectric layer (3) has a solid structure without cracks corresponding to the clefts (7) of the conductive layer (2). The construction according to the invention offers a reduction of the capillary effect and associated hysteresis up to a complete elimination of the effect in some embodiments of the invention.

8 Claims, 2 Drawing Sheets

CAPACITIVE HUMIDITY SENSOR CONSTRUCTION AND METHOD FOR MANUFACTURING THE SENSOR

BACKGROUND OF THE INVENTION

The present invention relates to a capacitive humidity sensor capable of being connected to a measurement device of dielectric factor.

The invention also concerns a method for manufacturing the humidity sensor.

The invention aims to achieve such a capacitive humidity sensor that has a fast response, and resistance to corrosion and good hysteresis characteristics.

DESCRIPTION OF THE BACKGROUND ART

Known from patent disclosure publication 71998 is a capacitor structure in which both one of the conductive layers and the dielectric layer are provided with clefts, which allow the dielectric material to communicate directly with ambient air. These clefts are fabricated by producing the conductive surface through vacuum deposition by evaporation from a material exhibiting so high internal stresses that its cracking also forms clefts in the adjoining dielectric layer.

When extending down to the dielectric layer these clefts, however, worsen the sensor's hysteresis and stability characteristics. It is well-known in the art that the so-called capillary condensation occurs in narrow gaps and capillaries at appreciably lower humidity than on a flat surface, and further, that capillary condensation is characterized by hysteresis (that is, condensation takes place at a higher RH level than the reverse effect of evaporation). For instance, condensation takes place in a cylindrical capillary closed at one end when the inner radius $r_k$ of the capillary is smaller than the value obtained from formula:

$$r_k = (2\gamma M)/(rRT \ln(P_s/P)),$$

where
- $\gamma$ = surface tension of water (72.75 dyn/cm at 20° C.)
- M = molecular weight of water (18.02 g/mol)
- r = density of water (1.00 g/cm$^3$)
- R = gas constant (8.31 J/(mol K))
- T = absolute temperature
- $P_s$ = partial saturation pressure of water For example, if the relative humidity is 90% (that is, $P_s/P = 1.1111$), condensation takes place in all capillaries having a radius of 0.01 μm or smaller.

Furthermore, clefts in the dielectric layer focus possible internal stresses to discrete points, which brings about a deleterious effect to the long-term stability of the sensor.

Moreover, contaminants accumulating in the clefts can have an effect on measurement results.

Due to the reasons considered above, it is preferable for the characteristics of the sensor to prevent the clefts of the electrode from extending into the dielectric layer in the manner described in the patent disclosure publication 71998, or alteratively, to fill the clefts in the dielectric layer with, for instance, a suitable plastic layer, whereby slowing in sensor response can be almost totally avoided by an appropriate material selection. The occurrence of clefts in the dielectric layer has, however, been inevitable when using conventional production methods.

SUMMARY OF THE INVENTION

Thus, it is an object of the present invention to overcome the drawbacks of conventional technology described above and to achieve an entirely novel capacitive humidity sensor and a method for the fabrication of the sensor.

The invention is based on providing at least one of conductive layers of the sensor with random pattern of clefts, while the adjoining dielectric layer is free from clefts.

More specifically, the capacitive humidity sensor in accordance with the invention is characterized by a dielectric layer having a solid structure without cracks corresponding to the clefts of the conductive layer.

Furthermore, the invention concerns a capacitor construction having a conductive layer with a random pattern of clefts, and said clefts are covered by a thin second layer of dielectric material.

The production method in accordance with the invention is characterized by producing the electrically conductive layer with inherently formed clefts from a material of high internal stresses using vacuum deposition onto a insulating layer of an dielectric material softened by a slowly-evaporating plasticizer, whereby the clefts forming in the conductive layer are prevented from cracking the dielectric layer.

More specifically, the method in accordance with the invention is characterized by the second conductive electrode being produced on the dielectric layer while the dielectric layer is still in a plasticized state, whereby the clefts formed on the second conductive layer are prevented from extending into the dielectric layer.

The invention provides significant benefits.

The sensor in accordance with the invention is capable of reducing the capillary effect and the resulting hysteresis, up to a complete elimination of the effect in some embodiments of the invention. The long-term stability of the sensor is further improved by the avoidance of cracks in the dielectric layer. Furthermore, the deterioration of sensor characteristics by contamination is reduced by virtue of the cleft-free dielectric layer.

If the conductive top layer is covered by a second dielectric layer, the formation of capillaries is entirely avoided. Selection of a material with high permeability to water yields an exceptionally first response.

Furthermore, if the second dielectric layer provides a good adhesion to the underlying layers, an extremely effective protection against corrosion is achieved.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is next examined in detail with the help of an exemplifying embodiment illustrated in the attached drawings which are given by way of illustration only, and thus are not limitative of the present invention.

DETAILED DESCRIPTION OF THE PREFERRED EMBODIMENTS

Figure 1:
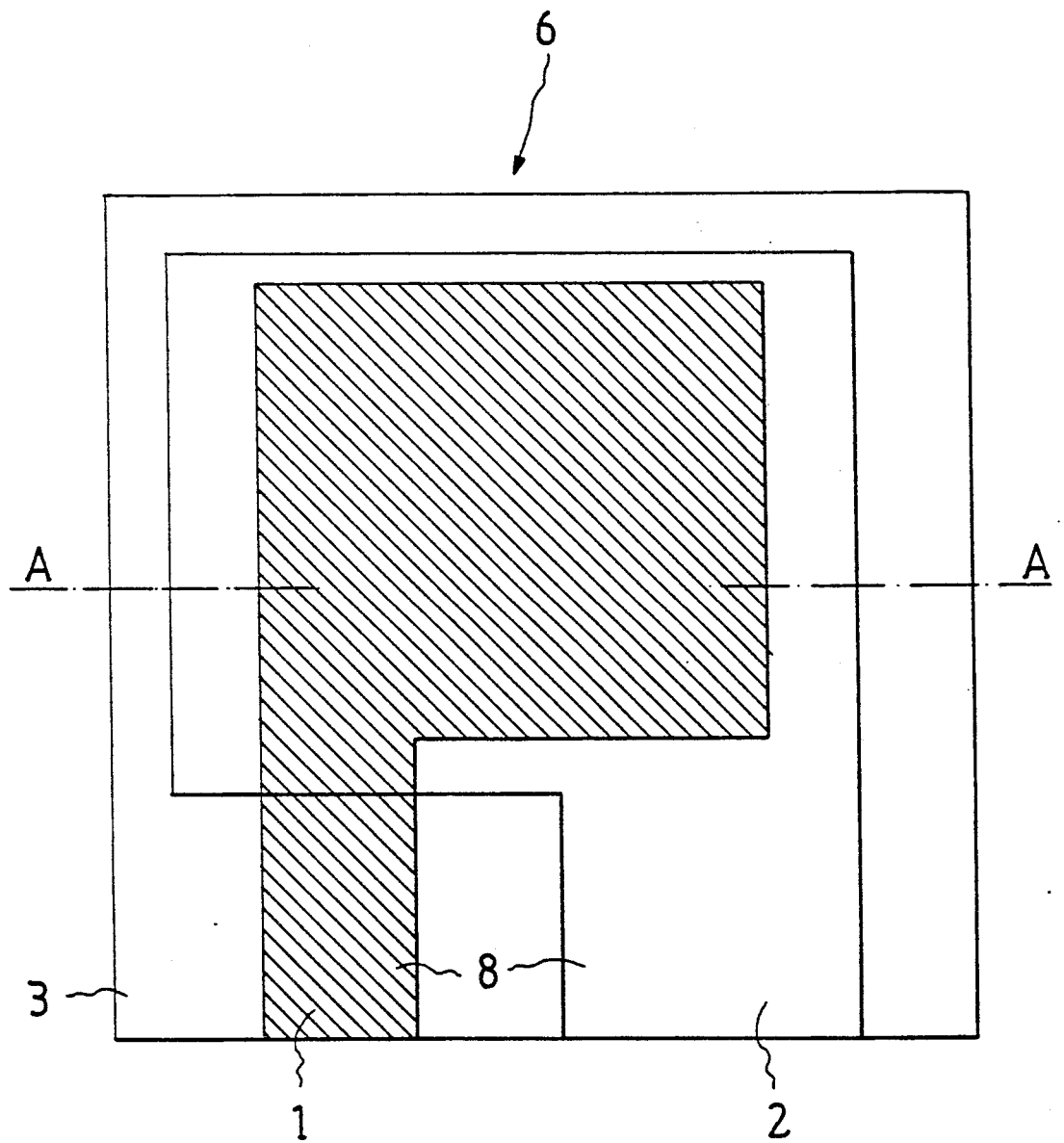
FIG. 1 shows a humidity sensor in accordance with the invention in a sectional top view.
Figure 2:
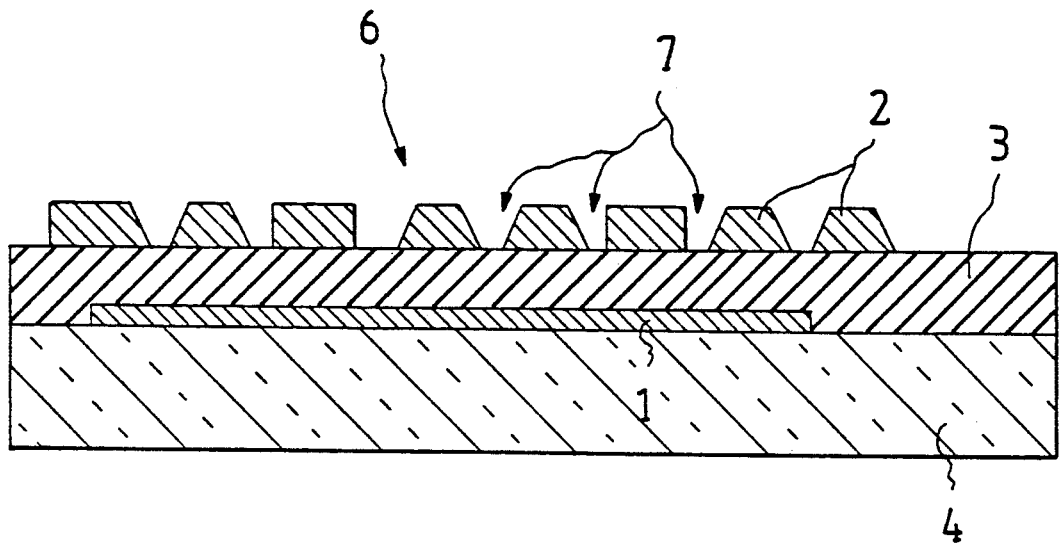
FIG. 2 shows a sectional side view of the capacitive humidity sensor illustrated in FIG. 1 taken along section A—A.

According to FIGS. 1 and 2, a sensor 6 can be fabricated onto, for instance, a lass substrate 4 so that a first conductive electrode 1, which can be an anodically oxidized tantalum layer for instance, is first placed closest to the substrate 4. Next, the first conductive electrode 1 is coated with a layer 3 of dielectric material, which typically is a suitable polymer such as cellulose acetate butyrate for instance. The dielectric layer 3 is covered by a second conductive electrode 2 from chromium for instance or other suitable material having a high resistance to wear. The second conductive electrode 2 must be of such a material that self-contracts under internal stresses when produced as a thin layer. This approach produces a plurality of clefts 7 in the second electrode 2. The contact leads (not shown) of a measurement device of dielectric factor are connected to electrodes 1 and 2 of the sensor at contact areas 8.

Figure 3:
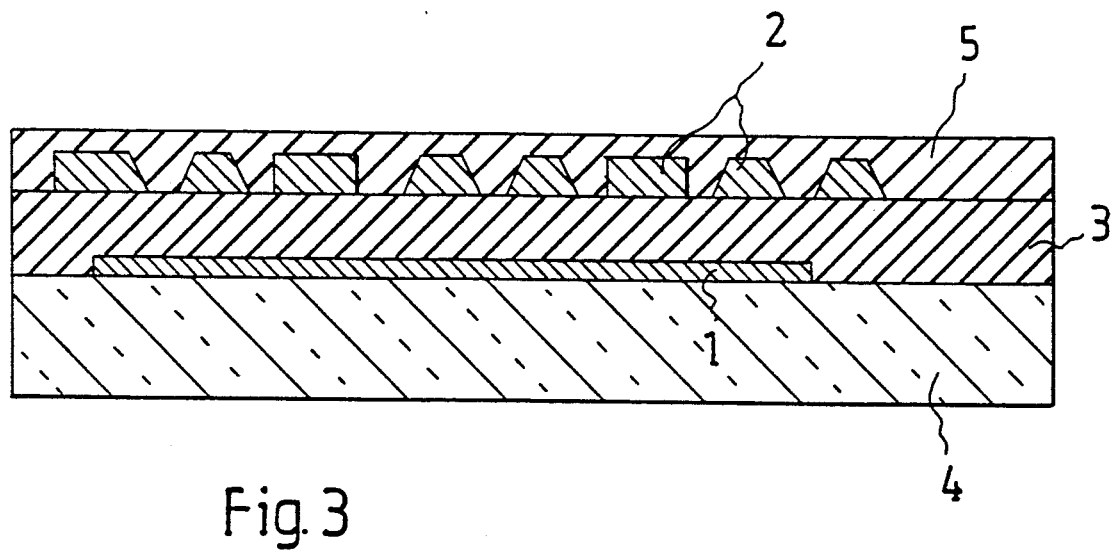
FIG. 3 shows the capacitive humidity sensor illustrated in FIG. 1 in a sectional side view after coating of the conductive layer with a dielectric layer.

According to FIG. 3 the second conductive electrode 2 of the sensor can be coated by a second dielectric layer 5 through which water vapour can diffuse to reach the first dielectric layer 3. Suitable materials for the second dielectric layer are, for instance, cellulose acetate and cross-linked polyvinyl pyrrolidone.

The preferred embodiment of the invention is characterized by a strong adherence of the second dielectric layer 5 to both the conductive electrode 2 with the clefts 7 and the first dielectric layer 3.

The sensor in accordance with the invention can be fabricated as follows:

The first electrode 1 is fabricated onto a glass substrate 4 using the methods of conventional thin-film technology, for instance, anodic oxidation. A polymer layer 3 is produced onto the first electrode 1 by, for instance, lifting the glass substrate 4 slowly from a liquid polymer, whereby a thin layer of plastic dissolved in the solvent remains on the glass substrate 4.

The solvent of the dielectric material can be, for instance, a mixture of NMP (N-methylpyrrolidone) and alcohol, wherein the NMP solvent forms the slowly evaporating component and the polymer is cellulose acetate butyrate. The polymer is predried for approx. 10 minutes at 150° C. temperature. The alcohol is thereby evaporated, but the polymer remains in a plasticized state by the effect of the NMP plasticizer. Next, a surface electrode 2 is deposited of, for instance, chromium onto the plasticized polymer layer. The electrode 2 is deposited up to approx. 0.1 . . . 1 μm thickness The sensor structure is postbaked for approx. 3 days at 150° C. temperature, whereby the NMP plasticizer is evaporated and the dielectric layer polymerizes to its final hardness.

Alternatively, the use of slowly evaporating solvent as plasticizing means of the dielectric layer can be omitted by maintaining the dielectric layer in a plastic state by means of elevated process temperature, whereby the sensor must be held, for instance, at 180° C. during the vapour deposition of the surface electrode 2. An essential condition is that the substrate temperature is above the glass transition temperature $T_g$ or the melting temperature.

According to FIG. 3, the second dielectric layer 5 is produced by immersion into liquid plastic using a comparable method with that used for the first layer 3. An essential condition is that the solvent used in the liquid polymer does not dissolve the first layer 3. Alternatively, the second dielectric layer can be produced by plasma polymerization from a suitable monomer (e.g., styrene), whereby a good adhesion between the layers is achieved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A capacitive humidity sensor capable of being connected to a measurement device of dielectric factor, said sensor comprising:
   a dielectric layer, whose dielectric factor changes in proportion to the moisture content absorbed in the layer; and
   at least two galvanically isolated conductive layers enclosing the dielectric layer, whereby one of the conductive layers of the capacitor construction is provided with a random pattern of clefts, which allow immediate communication of ambient air with the dielectric layer,
   the dielectric layer having a solid structure without cracks corresponding to the clefts of the conductive layer.

2. The humidity sensor in accordance with claim 1, wherein the conductive layer with the clefts is covered by a second and dielectric layer which is capable of allowing water vapour to diffuse into the first dielectric layer.

3. The humidity sensor in accordance with claim 2, wherein the second dielectric layer is firmly adhered both to the conductive electrode layer with the clefts and the first dielectric layer.

4. A method for manufacturing a capacitive humidity sensor, comprising the steps of:
   producing a first conductive electrode on an insulating substrate;
   producing a dielectric layer on the first conductive electrode; and
   forming a second conductive electrode on the dielectric layer from such material with a high resistance to wear that contracts under internal stresses when produced as a thin layer and forms clefts in the second conductive layer,
   the second conductive electrode being produced on the dielectric layer while the dielectric layer is still in a plasticized state, whereby the clefts formed on the second conductive layer are prevented from extending into the dielectric layer.

5. The method in accordance with claim 4, wherein the second electrode with the clefts is produced by vacuum evaporation onto the plasticized dielectric layer.

6. The method in accordance with claim 1, 2, 3, 4 or 5 wherein the dielectric layer is produced from a plastic material.

7. The method in accordance with claim 4 or 5, wherein the dielectric layer is held in a plasticized state by means of a slowly evaporating solvent such as NMP for instance.

8. The method in accordance with claim 1, 2, 3, 4 or 5 wherein the dielectric layer is held in a plasticized state with the help of elevated temperature, whereby the sensor is kept at a temperature above the glass transition temperature $T_g$ or the melting temperature, e.g., 180° C. during the processing of the second conductive electrode.

* * * * *